United States Patent [19]

Marconi et al.

[11] 4,353,996

[45] Oct. 12, 1982

[54] BIO-COMPATIBLE POROUS FIBRES AND MATERIALS FOR OCCLUDING BIOLOGICALLY INTERESTING SUBSTANCES, AND METHOD FOR THEIR MANUFACTURE

[75] Inventors: Walter Marconi, San Donato Milanese; Francesco Bartoli, Rome; Franco Morisi, San Giovanni in Persiceto; Francesco Pittalis, Rome, all of Italy

[73] Assignee: Snamprogetti, S.p.A., Milan, Italy

[21] Appl. No.: 189,817

[22] Filed: Sep. 23, 1980

Related U.S. Application Data

[63] Continuation of Ser. No. 885,195, Mar. 10, 1978, abandoned.

[30] Foreign Application Priority Data

Mar. 22, 1977 [IT] Italy ............................... 21482 A/77

[51] Int. Cl.$^3$ .............................................. A61K 31/74
[52] U.S. Cl. ...................................... 523/105; 424/27; 424/78; 424/81; 424/83; 523/112

[58] Field of Search ................ 260/9, 17.4 R; 424/16, 424/27, 78, 81, 83, 183

[56] References Cited

U.S. PATENT DOCUMENTS

| | | | |
|---|---|---|---|
| 3,674,901 | 7/1972 | Shepherd | 424/81 |
| 3,715,277 | 2/1973 | Dinelli | 195/63 |
| 3,846,353 | 11/1974 | Grotta | 260/17.4 R |
| 3,932,656 | 1/1976 | Ramwell | 424/16 |
| 4,031,201 | 6/1977 | Lostia | 424/27 |
| 4,073,723 | 2/1978 | Swank | 424/183 |
| 4,234,652 | 11/1980 | Vanoni | 424/81 |

*Primary Examiner*—Paul R. Michl
*Attorney, Agent, or Firm*—Morgan, Finnegan, Pine, Foley & Lee

[57] ABSTRACT

Fibres for biological uses can be produced by adding to a spinnable solution of a polymer selected from among many of the most common polymers and copolymers, a substance selected from among anti-platelet aggregation substances, anticoagulants and substances having a similar action. The substances can also be applied as a surface outer layer to articles made with the polymeric substances.

5 Claims, No Drawings

BIO-COMPATIBLE POROUS FIBRES AND MATERIALS FOR OCCLUDING BIOLOGICALLY INTERESTING SUBSTANCES, AND METHOD FOR THEIR MANUFACTURE

This is a continuation application of Ser. No. 885,195 filed on Mar. 10, 1978, now abandoned which claims the priority of Italian Patent Application No. 21482 A/77 filed Mar. 22, 1977.

This invention relates to novel bio-compatible polymeric materials and to the methods adopted for obtaining same; such methods essentially consisting in occluding within the fibrous material suitable agents or as an alternative, is coating, during the spinning stage, the fibrous material with a bio-compatible material. In the literature, and especially in the Italian Pat. No. 836 462, and the corresponding U.S. Pat. No. 3,715,277 owned by the Assignee hereof, it is known that it is possible to prepare filamentary structures by using solutions which contain such polymers as are capable of producing fibres, in which are dispersed solutions containing the products to be occluded in the form of tiny droplets of the order of magnitude of the emulsions.

An emulsion obtained in such a manner can be either dry-spun or wet-spun to give a fibre which has, in its interior, a number of tiniest hollows in which the occluded products are encased. Such products are seprated from the outside environment by the agency of a membrane which prevents the products concerned from exiting the hollow spaces, while concurrently permitting the free diffusion of the substances on which the occluded products are intended to be active.

Structures thus obtained have high activities due to the high surface-to-volume ratio and afford the possibility of encasing substances which possess even a not too high purity. By means of the methods which are the main subject-matter of the present invention, the present Applicants have succeeded in adjusting the composition of fibres, having properties which are akin to those referred to above, which are bio-compatible, that is to say capable of being introduced into a living organism or, anyhow, capable of being inserted into contact with blood, without involving hemorrhage or toxicity hazards, as is the case when using soluble anticoagulants.

Such fibres can also be used when it is required that such substances, as enzymes, antigens, antibodies or detoxicating agents be put into contact with blood, and these substances can be occluded in such fibres according to methods which are already known in the technical literature.

The methods suggested by ourselves, through which the fibres are rendered bio-compatible, are:

(a) adding, in the reaction mixture, to the polymeric solution, an appropriate anticoagulant agent and, when required, the substances to put into contact with blood;

(b) adding to the polymeric solution such reagents as to form, in the spinning stage, a bio-compatible surface layer. If so required, there can be introduced in the solution, also the substances to be put into contact with blood, said substances being susceptible of remaining occluded in the fibres.

Among the materials which can be used according to the present invention, there can be mentioned: the cellulosic polymers, the esterified, etherified and nitrated cellulosic polymers, the polyamides, the polymers and copolymers of acrylonitrile, butadiene and isoprene, acrylates and metacrylates, vinyl esters, vinyl chlorides, polymers or copolymers of vinylidene chloride, styrene, vinyl butyrate, gamma-methylglutamate, polyurethans and also mixtures of such polymers.

Among the products, which, when admixed with the above enumerated polymers, to permit the obtention of bio-compatible articles of manufacture, there can be cited agents which prevent the thrombocyte aggregation, such as 4,5-diphenyl-2-bis-(2-hydro-xyethyl)-amino oxazole, 4,8-dipiperidino-2,6-diethanolamino-pyrimido-(5,4d)-pyrimidine, derivatives of salicyclic acid such as aspirin and methyl salicylate and others. There can be used, for such purpose, polymers which are inherently bio-compatible, such as various kinds of polyurethans, used alone or in admixture with supporting polymer or as coatings for another polymer.

The ensuing examples should be regarded as illustrations but not limitations of the present invention.

EXAMPLE 1

Ten (10) grams of cellulose triacetate (Fluka) have been dissolved in 133 grams of methylene chloride (Carlo Erba, pure reagent) at room temperature. To the polymeric solution there has also be added 1 gram of 4,5-diphenyl-2bis-(2-hydroxyethyl)-amino oxazole prepared according to what is described in the literature: cfr. V. Rosnati, E. Marchetti, G. Mattalia, Journal Medical Chemistry, 11, pages 1092–1093, (1968).

To the polymeric solution, which has previously been cooled to zero centigrades, there have been added 20 grams of an aqueous solution which contains 30% of glycerol.

By stirring, an emulsion has been obtained which consists of droplets of the aqueous phase scattered in the polymeric phase and having diameters from 4 to 5 microns.

The emulsion has been allowed to stand for 20 mins., whereafter it has been poured in a steel cylinder, the latter being connected, at its top, to a nitrogen bottle and terminated, at the bottom, by a spinneret immersed in a toluene bath. By impressing a nitrogen pressure, the emulsion was caused to emerge from the spinneret in the toluene bath, wherein it was coagulated.

The filament thus obtained has been collected on a roller and treated with an air stream to remove toluene and methylene chloride.

A second preparation has been made with the same procedure by using for the formation of the emulsion a solution of concentrated invertase BDH instead of the water-glycerol solution. The activity unfolded by the invertase-containing fibre has been assayed by using as the substrate a 20% weight/volume solution of sucrose in a phosphate buffer (0.1 M, pH 4.5 at 25° C.).

The resultant activity was 30% of the total occluded activity and stood constant even after 30 days of continuous washing with a phosphate buffer (0.1 M, pH 4.5).

An intraveneous catheter (Wallace) of the length of 30 cm, inside diameter 0.69, outside diameter 1.14 mm, has been coated by a film of cellulose triacetate by immersion of the tube in a solution of the polymer in methylene chloride (2% conc.) (weight to weight basis) containing 4,5-diphenyl-2bis-(2-hydroxyethyl)-amino-oxazole in an amount equal to 10% relative to the triacetate of cellulose. On the catheter thus obtained, there have been wound in a homogeneous manner, along the entire length thereof, 60 milligrams of the fibre occluding the solution of water and glycerol.

The catheter has been inserted into the femoral vein of an average-build dog in general anaesthesia (Pentothal), free respiration.

A side-branch of the femoral vein has been isolated and the catheter has been introduced all the length throughout so as to have a predominant part of the catheter was floating in the iliac vein and in the inferior vena cava. The catheter end has been tied to the collateral branch of the femoral vein and covered by the muscle bundles. Finally a cutaneous suture has been made. During the operation and immediately thereafter, heparin has been administered to the animal to prevent vascular thrombi due to the surgical wounds.

The clinical status of the animal has been monitored for 90 days and periodical check-ups have been made of the following blood parameters: fibrinogenesis, platelet aggregation, prothrombine time, thromboelastogram, red cell count, bilirubin test.

The clinical data, tabulated in TABLE 1, show that for the entire duration of the test, the general conditions of the animal were normal. Finally, the catheters have been withdrawn and, after a careful scrutiny, they have been found fully deprived of thrombi. The post-mortem examination of the vein has evidenced the absence of vascular lesions.

TABLE 1

| Time days | Clinical condition | Fibrinogen mg/100 mls | BLOOD PARAMETERS Tensioelastogram r + X | am | Platelet aggregat. | Red cells % | Haemoglobin % | Bilirubin mg/100 mls |
|---|---|---|---|---|---|---|---|---|
| 1 | good | 240 | 10 | 72 | 38 | 44 | 14.0 | 0.56 |
| 7 | good | 250 | 10 | 70 | 42 | 46 | 14.2 | 0.62 |
| 30 | good | 210 | 12 | 74 | 40 | 45 | 13.8 | 0.64 |
| 60 | good | 220 | 9 | 72 | 35 | 46 | 13.9 | 0.60 |
| 86 | good | 230 | 10 | 71 | 38 | 43 | 14.4 | 0.60 |

EXAMPLE 2

There have been dissolved, in 133 grams of methylene chloride, 10 grams of cellulose triacetate and 1 gram of 4,4'-diaminodiphenyl methane. To the polymeric solution there have been added with stirring 20 grams of a 30% solution of water and glycerol.

Stirred has been continued until a homogeneous emulsion has been formed.

The emulsion has been transferred in the spinning tank as described in EXAMPLE 1, wherein the coagulation liquor was a solution of toluene containing 1% of polyethylene glycol bischloroformate (mol.wt. 325). During spinning, the diamine contained in the polymeric phase reacted with the bischloroformate dissolved in toluene and coated the fibre of triacetate of cellulose with a layer of polyurethan.

An intraveneous catheter such as that of EXAMPLE 1 above, has been coated by a film contained by a first immersion of the catheter in a 2% solution of triacetate of cellulose and 0.2% of 4,4'-diaminodiphenylmethane in methylene chloride, containing also 1% of polyethyleneglycolbischloroformate.

60 milligrams of fibre have been wound onto the catheter so as to wrap it completely the whole length throughout.

Then, the catheter has been inserted in the femoral vein of an average-size dog such as described in the EXAMPLE 1 hereinabove.

The test lasted 90 days.

TABLE 2 shows the values of the blood parameters as measured during the rest run.

Finally, after 90 days of stay in the vein, the catheter has been withdrawn according to the procedure outlined in EX. 1 hereof and it was found devoid of thrombi. The post-mortem examination of the femoral vein has proved the absence of vasal lesions.

TABLE 2

| Time days | Clinical condition | Fibrinogen mg/100 mls | Blood Parameters Tensioelastogram r + X | am | Platelet aggregat. | Red cells % | Haemoglobin % | Bilirubin mg/100 mls |
|---|---|---|---|---|---|---|---|---|
| 1 | good | 310 | 9 | 68 | 48 | 49 | 15.0 | 0.62 |
| 7 | good | 320 | 12 | 65 | 52 | 48 | 15.6 | 0.70 |
| 30 | good | 290 | 13 | 74 | 50 | 49 | 15.4 | 0.70 |
| 60 | good | 280 | 12 | 75 | 45 | 46 | 14.0 | 0.54 |
| 86 | good | 290 | 12 | 70 | 56 | 45 | 15.0 | 0.80 |

EXAMPLE 3

There have been dissolved, at room temperature, in 100 grams of methylene chloride, 15 grams of cellulose triacetate.

To the polymeric solution there have been added 1.5 grams of 4,5-diphenyl-2bis (2-hydroxyethyl)-amino oxazole. The solution has been allowed to evaporate until the solvent had completely be driven off.

A sheet has been obtained which had a thickness of 4 millimeters. The platelet adhesiveness test has been conducted with the method by Hellem, A. J. (Platelet adhesiveness in Von Willebrand's disease. A Study with a new Modification of the Glass Bead Filter Method, Scand., J. Haemat., 7, 374 (1970)), using 6 mls of the native blood of a healthy individual, drawn and immediately caused to flow through a glass bead column (AdeplatMascia Brunelli) by means of a pump delivering 4 mls per minute.

Then, the glass beads have been replaced by a piece of cellulose triacetate of the weight of 200 milligrams and the procedure described above has been repeated.

Platelet-counts have been made before and after the blood flow through the glass beads or the cellulosic material, the blood being collected in an aqueous solution containing bipotassium EDTA at the concentration of 6 grams in 10 mls.

The platelet-count has been effected with a phase-contrast microscope according to the procedure by Brecher and Cronkite (Morphology and enumeration of human-blood platelets, J. Appl. Physiol., 3, 365 (1950).

In the case of glass beads, the platelet adhesiveness was 78.8%; whereas in the case of the cellulosic material it has not been possible to measure the decrease of the platelets, that is, it was below the sensitivity of the measurement method.

EXAMPLE 4

20 grams of commercial PVC chips were milled on an openroll mill at the temperature of 120° C.-130° C. during 20 mins. To the polymer mass there has been added one gram of 4,5-diphenyl-2bis(2-hydroxyethyl-)amino oxazole. Upon cooling at room temperature a sheet has been obtained, having a thickness of 5 mm.

On 200 milligrams of the material thus obtained, the platelet adhesiveness has been measured with the method described in the previous EXAMPLE. Also in this case, no decrease of the platelets has been seen after the flow of the blood through the material concerned.

EXAMPLE 5

A tube made of poly-dimethylsiloxane having an inside diameter of 7 mm, an outside diameter of 9 mm and a length of 1 m, has been filled with a 1% acetonic solution of 4,5-diphenyl-2bis(2-hydroxyethyl) amino oxazole and then closed at both ends. After a 24-hour stay at room temperature, the solution had completcly been evaporated and the tube walls, viewed at the UV-lamp, were intensely and evenly fluorescent, this fact evidencing a regular distribution of the aggregation-preventing agent through the polymer.

A piece of the thusly treated tube and a similar reference tube have been subjected to the platelet adhesiveness test according to the method by A. J. Hellen (Platelet adhesiveness in Von Willebrand's disease. A Study with a New Modification of the Glass Bead Filter Method, in Scand. J. Haemat., 7, 374)1970)), using the native blood of an individual in good health, the blood being drawn and caused to flow through the tubes subjected to the test by the agency of a pump delivering 4 mls per minute. Platelet-counts have been made before and after the flow of the blood through the tubes, blood samples being collected in an aqueous solution containing dipotassium EDTA at a concentration of 6 milligrams in 10 milliliters. The platelet count has been made with a phase-contrast microscope according to the procedure by Brecher and Cronkite (Morphology and enumeration of human blood platelets, in J. Appl., Physiol., 3, 365 (1950).

In the case of the reference tube, the platelet adhesiveness was 58.5%. In the case of the treated tube, no appreciable decrease of the platelet number as present initially has been seen.

EXAMPLE 6

A tube of "Tygon" having an inside diameter of 7 mm, an outside diameter of 9 mm and a length of 1 m has been treated with the solution of the aggragation-preventing agent as in EXAMPLE 5. Then the tube has been subjected to the platelet adhesiveness test in comparison with an untreated tube according to the procedure disclosed in EXAMPLE 5. Also in this case, no appreciable decrease has been observed of the number of platelet in the treated tube, whereas in the untreated tube the adhesiveness has been found to be 48%.

We claim:

1. A bio-compatible synthetic fiber comprising a polymer selected from the group consisting of cellulosic polymers, esterified cellulosic polymers, etherified and nitrated cellulosic polymers, polyethylene, polyamides, vinyl chlorides, the polymers and copolymers of vinylidene chloride, styrene, vinylbutyrate and gamma methylglutamate, polymers and copolymers of acrylonitrile, butadiene and isoprene, acrylates and methacrylates, and vinyl esters, said polymer having occluded therein a bio-compatible platelet-aggregation preventing agent selected from the group consisting of 4,5-diphenyl-2-bis(2-hydroxyethyl) amino oxazole, 4,8-dipiperidino-2,6-diethanolaminopyrimido-(5,4d)-pyrimidine dicumarol, and derivatives of salicyclic acid.

2. A fiber as claimed in claim 1 wherein said polymer is cellulose triacetate and said bio-compatible material is 4,5-diphenyl-2bis-(2-hydroxyethyl)-amino oxazole.

3. A fiber as claimed in claim 1 wherein said polymer is polyvinylchloride and said bio-compatible material is 4,5-diphenyl-2bis(2-hydroxyethyl) amino oxazole.

4. A method of producing a bio-compatible synthetic fiber which comprises adding a platelet-aggregation preventing agent selected from the group consisting of 4,5-diphenyl-2-bis (2-hydroxyethyl) amino oxazole, 4,8-dipiperidino-2,6-diethanolaminopyrimido-(5,4d)-pyrimidine dicumarol, and derivatives of salicylic acid to a solution containing a polymer selected from the group consisting of cellulosic polymers, esterified cellulosic polymers, etherified and nitrated cellulosic polymers, polyethylene, polyamides, vinyl chlorides, the polymers and copolymers of vinylidene chloride styrene, vinylbutyrate and gamma methylglutamate polymers and copolymers of acrylonitrile, butadiene and isoprene, acrylates and methacrylates, and vinyl esters to form a mixture, adding a bio-compatible surface layer forming reagent to said mixture to thereby form a spinnable solution and spinning said solution to thereby form said bio-compatible synthetic fiber.

5. The method of producing a bio-compatible synthetic fiber as claimed in claim 4, which includes adding 4,4'-diamino-diphenylmethane to said solution and reacting said 4,4'-diphenylmethane and polyethylene glycol bis-chloroformate during said spinning step to form a bio-compatible polyurethane, and causing said polyurethane to coat said fibers.

* * * * *